United States Patent [19]

Heim

[11] Patent Number: 4,765,962

[45] Date of Patent: Aug. 23, 1988

[54] GAS TESTING VIAL

[75] Inventor: Ulrich Heim, Reinfeld, Fed. Rep. of Germany

[73] Assignee: Drägerwerk AG, Fed. Rep. of Germany

[21] Appl. No.: 862,701

[22] Filed: May 13, 1986

[30] Foreign Application Priority Data

May 14, 1986 [DE] Fed. Rep. of Germany ....... 3517324

[51] Int. Cl.⁴ .................... G01N 21/77; G01N 31/22; G01N 33/497

[52] U.S. Cl. ........................................ 422/59; 422/60; 422/86; 422/88; 436/169; 436/170; 436/900

[58] Field of Search ....................... 422/56, 58, 59, 60, 422/61, 85, 86, 88, 84; 436/169, 170, 900

[56] References Cited

U.S. PATENT DOCUMENTS

| | | | |
|---|---|---|---|
| 3,437,449 | 4/1969 | Luckey | 422/85 |
| 3,510,263 | 5/1970 | Hach | 436/163 |
| 3,993,451 | 11/1976 | Verbeck | 422/57 |
| 4,059,407 | 11/1977 | Hochstrasser | 422/56 |
| 4,554,133 | 11/1985 | Leichnitz | 422/86 |

FOREIGN PATENT DOCUMENTS 92101 10/1983 European Pat. Off. ............. 422/58

Primary Examiner—Barry S. Richman
Assistant Examiner—C. M. Delahunty
Attorney, Agent, or Firm—McGlew and Tuttle

[57] ABSTRACT

A test vial for the detection of gas components in air, containing a packing changing along the longitudinal axis of the test vial is improved in such a manner that, at a constant flow resistance, a sensitivity for the hazardous substance to be detected is obtained, which varies along the test vial. The provision is made that the packing consists of a combination of applied indicator and carrier substance at ratios varying along the longitudinal axis.

10 Claims, 1 Drawing Sheet

GAS TESTING VIAL

BACKGROUND OF THE INVENTION

Field of the Invention

The invention relates in general to gas testing devices and in particular to a new and useful test vial for the detection of gas components in the air, with a packing that varies along the longitudinal axis of the test vial.

Such test vials have become known from the U.S. Pat. No. 3,620,677. There, a granular packing impregnated with a color reagent is contained in an envelope that changes shape along its lateral axis. With this the progression of the zone of reaction needed for the detection of a gaseous hazardous substance can be calibrated by suitable selection of the packing cross section and its change along the longitudinal axis of the test vial in such a manner that, at different gas concentrations, the discolored area has a definite specific relation to the amount of the detected hazardous substance. A test vial which shall permit the desired accuracy of measurement even in different measuring ranges of the test vial, can be produced by giving the packing a suitable shape.

Since the known test vials have different cross sections of the area, with impregnated packing material, through which the stream of gas containing the hazardous substance is flowing and which are arranged in succession along the axis of the test vial, the gas to be analyzed will have various flow rates and profiles. This irregular flow, due to the not entirely uniform packing of the carrier material, results in locally different air resistances. Because of the changing flow rates there is no guarantee that the necessary time of direct contact of the hazardous substance to be detected with the impregnated packing is maintained in all parts within the test vial to bring about a quantitative reaction of the indicator. The desired accuracy of measurement is thereby destroyed again.

SUMMARY OF THE INVENTION

The purpose of the present invention is envisioned as an improvement in a test vial of the known type, which results in a variable sensitivity for the hazardous substance to be detected along the test vial, while the flow resistance remains steady.

The problem is solved by using a packing consisting of a composition of applied indicator and carrier substance arranged at ratios varying along the longitudinal axis.

This arrangement keeps the flow resistance in the test vial through the packing constant, as the amount of test air needed for the detection of the amount of hazardous substance flows through. The total amount of test air is distributed, depending on requirements and desired accuracy of detection, over varying spread out amounts of indicator, by suitable variation of the ratios of indicator to carrier substance. The change in the composition of the ratios of applied indicator to carrier substance is obtained, for example, by impregnating the entire carrier substance continuously with the indicator, but varying the latter's levels of concentration along a longitudinal axis. The carrier substance can also be impregnated with a constant concentration of indicator, but then the impregnated areas on the carrier substance along the longitudinal axis have different cross sections.

The use of a granular carrier substance offers the advantage of a varying indicator content by adjusting the mixing ratio of unimpregnated carrier substance and carrier substance impregnated with constant amounts of indicator. This arrangement has the advantage of requiring only two types of packing material, i.e., unimpregnated carrier substance and carrier substance impregnated with constant amounts of indicator, for the preparation of such a test vial. Every desired concentration of indicator in the packing can be obtained by adjusting varying mixing ratios.

While the packing materials are arranged in areas separated from one another, the impregnated carrier substance can then be located in higher concentration in the visible area to improve the reading accuracy, especially for the detection of small amounts of hazardous substances.

The impregnated area of the packing can be shaped to advantage by adding a binder to the packing. With this process, the impregnated area of the packing in the test vial can be formed first and will retain its shape after curing the binder, so that the remaining empty spaces or zones can then be filled with the unimpregnated carrier substance.

The impregnated area can be separated from the unimpregnated area by using an intermediate layer consisting of a lattice network or also a porous, fibrous material that does not have a disturbing effect on the flow resistance along the test vial. The intermediate layer can be inserted to advantage as a preformed separator into the still empty test vial.

Accordingly it is an object of the invention to provide a test vial for the detection of gas components in air which includes a detection packing positioned in a glass container which has a detection material concentration which varies from one end to the other through which the gas to be detected is directed.

A further object of the invention is to provide a detection vial for gas substances which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
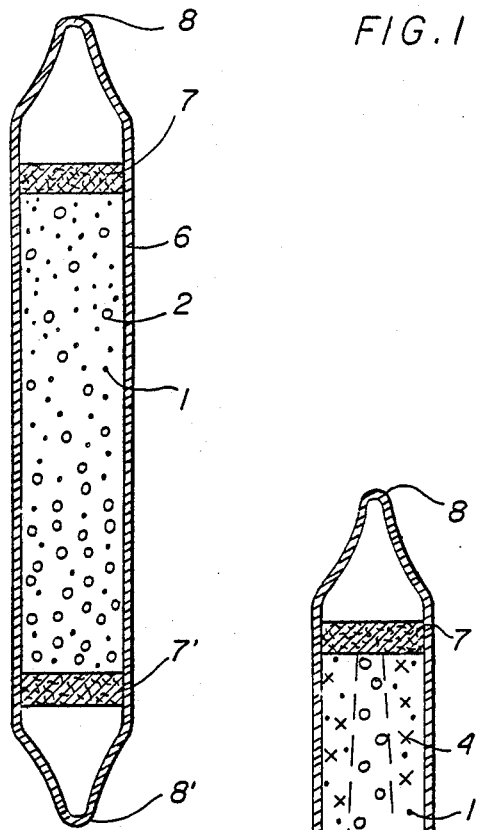
FIG. 1 is an axial sectional view of the test vial constructed in accordance with the invention.

Referring to the drawings in particular the invention embodied therein comprises a tube or vial 6 which is packed with a material between separators 7 and 7' ranged between breakable end portions 8 and 8' and providing a path through which the gas to be tested is directed. A glass tube or vial 6 shown in FIG. 1 has a filling consisting of a mixture of unimpregnated carrier substance 2 and impregnated carrier substance 1 at different ratios.

Glass vial 6 contains two fleece-like or fiber separators 7 between its end points 8, 8' which can be broken off. The packing consists of impregnated granular carrier substance 1 (represented by dots) and unimpregnated granular carrier substance 2 (represented by open circles). The amount of impregnated carrier substance 1 compared to substance 2, increases continuously from bottom to top in the shown mixture of FIG. 1. That is the ratio of substance 1 to substance 2 increases from bottom to the top of the tube 6.

Figure 2:
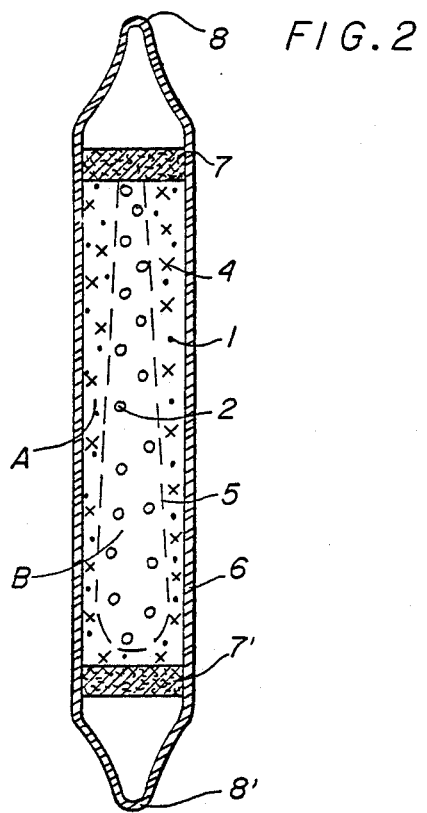
FIG. 2 is a similar view of another embodiment of the test vial with a cutaway view of an intermediate layer.

In FIG. 2, a glass vial 6 is shown which has a packing consisting of an area or region A with impregnated carrier substance 1 and an area or region B with unimpregnated carrier substance 2, arranged between its separators 7. The regions A and B are separated by the intermediate layer 5. The impregnated carrier substance 1 in regions A contains an additional binder 4, represented in FIG. 2 by crosses. The fleece-like intermediate layer 5 is shown represented by a broken line as a gas-permeable hollow body. As shown in FIG. 2, region A is near the walls of tube 6 and forms a hollow area which is occupied by region B. The cross sectional area of region A substantially increases from the bottom of the tube to the top thereof while conversely the region B decreases in cross sectional area from the bottom of the tube to the top thereof. This is excluding a small part of region A which covers the lower separation 7'.

A test vial according to FIG. 2 can be prepared, for example, by first inserting intermediate layer 5 in the empty glass vial and then filling area A with impregnated carrier substance 1 mixed with a binder 4. After drying binder 4, the carrier substance 1 in area A has a stable consistency. Now, intermediate layer 5 may be removed and the remaining space of area B filled with unimpregnated granular carrier substance 2, or intermediate layer 5 may remain inserted as a wall covering for area A, in which case the space of area B can be filled with an unimpregnated granular carrier substance 2.

What is claimed is:

1. A test vial for the detection for gas components in air comprising: a tube having opposite closed ends which are openable to permit a passage of air through said tube; a pair of spaced apart separators in said tube, each separator being adjacent to one of said closed ends and being pervious to air passing through said tube; an amount of impregnated granular carrier substance in said tube between said separators, said impregnated granular carrier substance being impregnated with indicator material which changes color upon being exposed to the gas component; and an unimpregnated granular carrier substance in said tube between said separators, said impregnated and said unimpregnated granular carrier substances substantially filling the volume in said tube between said separators, the ratio between amounts of impregnated and unimpregnated carrier substance, for a tube cross section per unit length, changing generally continuously from one of said separators to other of said separators.

2. A test vial according to claim 1 wherein said impregnated and unimpregnated granular carrier substances are intermixed across each tube cross section.

3. A test vial according to claim 2 wherein each of said separators is made of porous fiber material.

4. A test vial according to claim 3 wherein each of said closed ends is breakable.

5. A test vial according to claim 1 wherein said amount of impregnated granular carrier substance is confined to a separate region in said tube than said amount of unimpregnated carrier substance.

6. A test vial according to claim 5 wherein said tube has a side wall, said region of said impregnated carrier substance extends along and is adjacent said side wall to form an outer region which defines an inner space, said region of said unimpregnated carrier substance fills said inner space defined by said outer region to from an inner region, the cross sectional area of said outer region increases along the length of said tube; from one of said separators to the other of said separators and the cross sectional area of said inner region decreases along the length of said tube from said one of said separators to said other of said separators.

7. A test vial according to claim 6 including a binder mixed with said impregnated granular carrier substance in said outer region for holding said impregnated carrier substance in said outer region to form said hollow inner region which is filled with said impregnated carrier substance.

8. A test vial according to claim 7 including an intermediate fleece-like intermediate layer positioned and arranged in said space to separate said outer region from said inner region.

9. A test vial according to claim 7 wherein each of said separators is made of porous fiber material.

10. A test vial according to claim 9 wherein each of said closed ends is breakable.

* * * * *